US010406096B2

(12) United States Patent
Chon et al.

(10) Patent No.: US 10,406,096 B2
(45) Date of Patent: Sep. 10, 2019

(54) **COMPOSITIONS COMPRISING EXTRACTS OF *BURSERA SIMARUBA***

(71) Applicant: Johnson & Johnson Consumer Inc., Skillman, NJ (US)

(72) Inventors: Suhyoun Chon, Princeton, NJ (US); Ya-Ping Hu, Somerset, NJ (US); Khalid Mahmood, South Hadley, MA (US); Apostolos Pappas, Bridgewater, NJ (US); Ramine Parsa, Lawrenceville, NJ (US); Kurt A. Reynertson, Hopewell, NJ (US); Michael D. Southall, Pennington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 324 days.

(21) Appl. No.: 15/403,364

(22) Filed: Jan. 11, 2017

(65) Prior Publication Data

US 2017/0119659 A1    May 4, 2017

Related U.S. Application Data

(62) Division of application No. 13/891,240, filed on May 10, 2013, now Pat. No. 9,579,278.

(51) Int. Cl.

| | | |
|---|---|---|
| *A61K 36/00* | (2006.01) | |
| *A61K 8/97* | (2017.01) | |
| *A61Q 19/00* | (2006.01) | |
| *A61Q 19/08* | (2006.01) | |
| *A61Q 19/10* | (2006.01) | |
| *A61Q 9/02* | (2006.01) | |
| *A61Q 19/02* | (2006.01) | |
| *A61Q 5/02* | (2006.01) | |
| *A61Q 5/06* | (2006.01) | |
| *A61Q 5/12* | (2006.01) | |

(52) U.S. Cl.
CPC .................. *A61K 8/97* (2013.01); *A61Q 9/02* (2013.01); *A61Q 19/00* (2013.01); *A61Q 19/007* (2013.01); *A61Q 19/02* (2013.01); *A61Q 19/08* (2013.01); *A61Q 19/10* (2013.01); *A61Q 5/02* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 4,337,370 | A | 6/1982 | Takisawa et al. |
| 6,746,695 | B1 | 6/2004 | Martin |
| 6,894,077 | B2 | 5/2005 | Suzuki |
| 6,932,975 | B2 | 8/2005 | Ishikawa et al. |
| 7,442,391 | B2 | 10/2008 | Kognanov |
| 7,473,435 | B2 | 1/2009 | Kognanov |
| 7,537,791 | B2 | 5/2009 | Kognanov |
| 8,658,223 | B2 | 2/2014 | Willis et al. |
| 2003/0060379 | A1 | 3/2003 | Souter et al. |
| 2004/0131567 | A1 | 7/2004 | Wilkins, Jr. |
| 2005/0226834 | A1 | 10/2005 | Lambino et al. |
| 2006/0141014 | A1 | 6/2006 | Eknoian et al. |
| 2006/0189512 | A1 | 8/2006 | Ehrenkranz |
| 2007/0053945 | A1 | 3/2007 | Bass |
| 2007/0196523 | A1 | 8/2007 | Koganov |
| 2009/0170809 | A1 | 7/2009 | Vera et al. |
| 2009/0241242 | A1 | 10/2009 | Beatty et al. |
| 2015/0024074 | A1 | 1/2015 | Batchvarova |

FOREIGN PATENT DOCUMENTS

| | | |
|---|---|---|
| CN | 1254581 A | 11/1998 |
| FR | 1155973 A | 1/2011 |
| JP | 2000198714 A | 1/1999 |
| JP | 2000281553 A | 10/2000 |
| JP | 2002255734 A | 3/2001 |
| JP | 2001192338 A | 7/2001 |
| JP | 2003146902 A | 11/2001 |
| JP | 2003045856 A | 4/2003 |
| JP | 2005298441 A | 4/2004 |
| JP | 2007119432 A | 1/2005 |
| JP | 2007145725 A | 11/2005 |
| JP | 2006188494 A | 7/2006 |
| JP | 2010195723 A | 2/2009 |
| JP | 200991260 A | 4/2009 |
| WO | WO 1996/03033 A | 2/1996 |

OTHER PUBLICATIONS

Abad, M., et al. "Antiinflammatory Activity of Some Medicinal Plant Extracts from Venezuela", Journal of Ethnopharmacology, vol. 55 (1996), pp. 63-68.
Akerlof, G., "Dielectric Constants of Some Organic Solvent-Water Mixtures at Various Temperatures", Journal of American Chemical Society, vol. 54, No. 11 (Nov. 1932), pp. 4125-4139.
Ando, H., et al., "Quasi-Drugs Developed in Japan for the Prevention or Treatment of Hyperpigmentary Disorders", International Journal of Molecular Sciences, vol. 11 (2010) pp. 2566-2575.
Bork, P., et al., "Nahua Indian Medicinal Plants (Mexico): Inhibitory Activity on NF- kB as an Anti-Inflammatory Model and Antibacterial Effects", Phytomedicine, vol. 3 (3) (1996) pp. 263-269.
Camporese, A., et al., "Screening of Anti-Bacterial Activity of Medicinal Plants from Belize (Central America)", Journal of Ethnopharmacology, vol. 87 (2003), pp. 103-107.
Carretero, M., et al. "Preliminary Study of the Anti-Inflammatory Activity of Hexane Extract and Fractions from *Bursera simaruba* (Linnea) Sarg. (Burseraceae) Leaves", Journal of Ethnopharmacology, vol. 116 (2008) pp. 11-15.
Ciccio, J, et al., "Isolation of the Lignan Yatein From Bark of Bursera Simaruba", Ingenieria y Ciencia Quimica (1995), vol. 15(1), p. 20-21 (Abstract Provided).
De Rodriguez, D., et al. "An Overview of the Antimicrobial Properties of Mexican Medicinal Plants", Advances in Phytomedicine (2006), pp. 325-377.

(Continued)

*Primary Examiner* — Qiuwen Mi

(57) ABSTRACT

The present invention relates to a skin care composition comprising an extract of *Bursera simaruba* seeds and a cosmetically acceptable topical carrier. Such composition is useful for improving skin barrier function and moisturization as well as improving signs of skin aging.

11 Claims, No Drawings

(56) References Cited

OTHER PUBLICATIONS

Edwards, Honest Nutrition; Trafford Publishing, USA; 2007, p. 220.
European Search Report completed Sep. 19, 2014 for corresponding Application No. EP14167945.
Hamamoto, Y., et al. "Inhibitory Effect of Azelastine, a Potent Antiallergic Agent, on Release of Tumor Necrosis Factor-a From Activated Human Peripheral Blood Mononuclear Cells and U937 Cells", Experimental Dermatology, vol. 2, (1993) pp. 231-235.
Junor, G-0, et al., "Investigation of Essential Oil Extracts from Four Native Jamaican Species of *Bursera* for Antibacterial Activity", West Indian Medical Journal, vol. 56 (1), (2007) pp. 22-25.
Junor, G.-0., et al. The Chemical Composition of the Essential Oils from the Leaves, Bark and Fruits of *Bursera simaruba* (L.) Sarg. From Jamaica, Journal of Essential Oil Research, vol. 2 (Sep./Oct. 2008) pp. 426-429.
Maldini, M., et al. "Phenolic Compounds from *Bursera simaruba* Sarg. Bark: Phytochemical Investigation and Quantitative Analysis by Tandem Mass Spectrometry", Phytochemistry, vol. 70 (2009) pp. 641-649.
Maldini, M., et al. "ESI-MS, ESI-MS/MS Fingerprint and LLC-ESI-MS Analysis of Proathocyanidins from Bursera simaruba Sarg Bark", Natural Product Communications, vol. 4, No. 12, (2009) pp. 1671-1674.
Noguera, B., et al. "Anti-Inflammatory Activity of Leaf Extract and Fractions of Bursera Simaruba (L.) Sarg (Burseraceae)", Journal of Ethnopharmacology, vol. 92 (2004) pp. 129-133.
Peraza-Sanchez, S., et al., "A New Triterpene From the Resin of Bursera Simaruba", Journal of Natural Products, vol. 58, No. 2, (Feb. 1995) pp. 271-274.
Peraza-Sanchez, S., et al. "Isolation of Picropolygamain From the Resin of Bursera Simaruba", Journal of Natural Products, vol. 55, No. 12 (Dec. 1992), pp. 1768-1771.
Rosales, K., et al., "The Volatile Oil of the Fruits of Bursera Simaruba", Ingenieria y Ciencia Quimica (2002), vol. 20(2), pp. 60-61 (Abstract Provided).
Rosas-Pinon, Y., et al, "Ethnobotanical Survey and Antibacterial Activity of Plants Used in the Altiplane Region of Mexico for the Treatment of Oral Cavity Infections", Journal of Ethnopharmacology, vol. 141 (2012), pp. 860-865.
Sanchez-Medina, A., et al., Evaluation of Biological Activity of Crude Extracts from Plants Used in Yucatecan Traditional Medicine Part 1. Antioxidant, Antimicrobial and β-Glucosidase Inhibition Activities, Phytomedicine, vol. 8, No. 2, pp. 144-151 (2001).
Sarker Ed. et al. Natural Products Isolation, 2nd Edition (Methods in Biotechnology, vol. 20) Humana Press Inc., Totowa, NJ . 2006 xii + 515 pp. pp. 27-46.
Solano, F., et al., "Hypopigmenting Agents: An Updated Review on Biological, Chemical and Clinical Aspects", Pigment Cell Research, vol. 19 (2006), pp. 550-571.
Sosa, S., et al. "Screening of the Topical Anti-Inflammatory Activity of Some Central American Plants", Journal of Ethnopharmacology, vol. 81 (2002) 211-215.
Sylvestre, M., et al., Volatile Leaf Constituents and Anticancer Activity of Bursera simaruba (L.) Sarg. Essential Oii,(Natural Product Communications, vol. 2, No. 12, (2007) pp. 1273-1276.
Wagner, D., "Rainforest Remedies That May be Useful for Today's Common Ailments", Point of Light Magazine, (Winter 2000-2001).
Yasunaka, K. et al., "Antibacterial Activity of Crude Extracts from Mexican Medicinal Plants and Purified Coumarins and Xanthones", Journal of Ethnopharmacology, vol. 97 (2005) pp. 293-299.

COMPOSITIONS COMPRISING EXTRACTS OF *BURSERA SIMARUBA*

This application is a divisional of U.S. application Ser. No. 13/891,240 filed on May 10, 2013, the complete disclosure of which is hereby incorporated herein by reference for all purposes.

FIELD OF INVENTION

The present invention relates to compositions comprising plant extracts for use on skin. More specifically, it relates to compositions comprising extracts of *Bursera simaruba* for improving the condition and appearance of the skin.

DESCRIPTION OF RELATED ART

*Bursera simaruba* is native to tropical regions of the Americas, right from southeastern United States (southern Florida), south through Mexico, the Caribbean to Brazil and Venezuela (northern South America), where it grows wild in abundance. It is commonly grown as an ornamental; the tree has an elegant habit and is salt and wind-tolerant. The shiny-red peeling bark gives it the name "tourist tree" because it resembles the sun-burnt, peeling skin of tourists. It is fast-growing, and the lumber can be used in construction. It is also known by the common name "gumbo limbo."

The sap produces a fragrant resin. Branches are often cut and stuck into the soil, where they will root and create living fences. The tree resin can be used as a wood varnish, glue or incense. Birds eat the seeds, which aides in the dispersal of the wild populations. The resin is also used as a treatment for gout, while the leaves are brewed into a medicinal tea (Abad M J; Bermejo P; Carretero E; Martinez-Acitores C; Noguera B; Villar A; Journal of Ethnopharmacology (1996), 55(1), 63-8). The essential oils from the *Bursera simaruba* leaves are found to have anti-cancer activity (Sylvestre, Muriel; Longtin, Andre Pichette Angelique; Legault, Jean; Natural Product Communications (2007), 2(12), 1273-1276).

The ethanolic extracts of the plant are used for treating dental diseases (Rosas-Pinon Yazmin; Mejia Alicia; Diaz-Ruiz Gloria; Aguilar Maria Isabel; Sanchez-Nieto Sobeida; Rivero-Cruz J Fausto; Journal of Ethnopharmacology (2012), 141(3), 860-5). Various parts of the plant are also reported to have anti-bacterial activity (Camporese A; Balick M J; Arvigo R; Esposito R G; Morsellino N; De Simone F; Tubaro A; Journal of Ethnopharmacology (2003), 87(1), 103-7).

Jungle Salve is a topical composition made from gumbo limbo bark said to be useful for treating psoriasis, eczema, insect bites and fungus (Wagner, Point of Light Magazine, Winter 2000-2001; http://nutrifarmacy.pdiwebdesign.com/articles/polwinter00.html).

The present invention relates to applicant's discovery that extracts of *Bursera simaruba* seeds are beneficial for use in compositions for skin and provide significant and unexpected benefits for skin including enhancing barrier protection and skin moisturization and improving the signs of aging.

SUMMARY OF THE INVENTION

The present invention is directed to a skin care composition comprising an extract of *Bursera simaruba* seeds and a cosmetically acceptable topical carrier.

The invention also provides a method of improving the barrier function and moisturization of skin, comprising topically applying to skin in need of improving skin barrier function and moisturization a composition comprising an extract of *Bursera simaruba* seeds and a cosmetically acceptable topical carrier.

A method of improving a sign of skin aging, comprising topically applying to skin in need of treatment for signs of skin aging a composition comprising an extract of *Bursera simaruba* seeds and a cosmetically acceptable topical carrier.

DESCRIPTION OF THE INVENTION

All percentages listed in this specification, unless otherwise stated, are weight percentages based on the total weight of composition.

As used herein, "skin in need of improving skin barrier function and moisturization" means a skin that is, but not limited to, lacking in moisture, lacking in sebum, cracked, dry, itchy, scaly, xerodermic, dehydrated, lacks suppleness, lacks radiance, dull, or lacks lipids.

As used herein, "skin in need of treatment for signs of skin aging" means a skin that is, but not limited to, sagging, loose, lax, rough, wrinkly, thinned, or uneven. Improving a sign of skin aging means improving the firmness of skin, improving the texture of skin, improving the appearance of wrinkles in skin, improving the skin tone, or the treating external aggressions in skin.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See Handbook of Non-Invasive Methods and the Skin, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle and fine line formation in skin.

As used herein, "treating external aggressions in skin" means the reduction or prevention of the damage from external aggressions in skin. Examples of external aggressions include, but are not limited to, damage to the skin from the use of cleansers (e.g., topical cleansers containing surfactants), make-up, shaving as well as environmental damage such as from UV light (e.g., sun damage from sunlight or damage from non-natural sources such as UV lamps and solar simulators), ozone, exhaust, pollution, chlorine and chlorine containing compounds, and cigarette smoke. Effects of external aggressions on the skin include, but are not limited to, oxidative and/or nitrosative damage to and modifications on lipids, carbohydrates, peptides, proteins, nucleic acids, and vitamins. Effects of external aggressions on the skin also include, but are not limited to, loss of cell viability, loss or alteration of cell functions, and changes in gene and/or protein expression.

As used herein, "improving the skin tone" means the lightening of the appearance of the skin (e.g., lightening pigmented marks or lesions, reducing skin sallowness, and/or evening the color of the skin).

As used herein, the term "lightening the appearance of skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the appearance of skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the appearance of skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the COLIPA GUIDELINE: GUIDELINE FOR THE COLORIMETRIC DETERMINATION OF SKIN COLOUR TYPING AND PREDICTION OF THE MINIMAL ERYTHEMAL DOSE (MED) WITHOUT UV EXPOSURE published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof.

As used herein, a composition that is "essentially free" of an ingredient means the composition has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. contains none of that ingredient.

As used herein, "cosmetically/dermatologically acceptable" means suitable for use in contact with tissues (e.g., the skin or hair) without undue toxicity, incompatibility, instability, irritation, allergic response, and the like.

As used herein, the term "safe and effective amount" means an amount sufficient to induce the desired effect, but low enough to avoid serious side effects. The safe and effective amount of the compound, extract, or composition will vary with, e.g., the age, health and environmental exposure of the end user, the duration and nature of the treatment, the specific extract, ingredient, or composition employed, the particular pharmaceutically-acceptable carrier utilized, and like factors.

As described herein, applicants have discovered that extracts of *Bursera simaruba* seeds and topical compositions containing them provide unexpectedly good skin barrier function, skin moisturization, and skin anti-aging benefits. In particular, applicants have discovered that extracts of *Bursera simaruba* seeds provide a significant increase in ceramide levels in the skin. Applicants have also discovered that topical application of extracts of *Bursera simaruba* seeds provide enhancement of endogenous hyaluronic acid levels. As shown in the Examples, the present seed extracts provide significant benefits in improving the skin barrier function, moisturization and anti-aging benefits compared to other extracts of *Bursera simaruba*.

Seed is the propagative part of the plant specifically the fertilized, matured ovule of a plant. Seeds are preserved parts of the plant especially for growing a crop. Seeds are also consumed for their fat and protein contents collectively nutrient contents.

The seed or fruit of *Bursera simaruba* is a round drupe-like capsule approximately 1 cm in diameter that ripens from green to red; when dry, it dehisces along 3 angles to release a single diamond-shaped pyrene-type seed lacking endosperm. Seeds are covered by a reddish, lipid-rich pseudaril.

Bark is the outermost layer of stems and roots of woody plants. Bark refers to all the tissues outside of the vascular cambium. It overlays the wood. The inner bark, which in older stems is living tissue, includes the innermost area of the periderm. The outer bark in older stems includes the dead tissue on the surface of the stems, along with parts of the innermost periderm and all the tissues on the outer side of the periderm. The inner bark of *Bursera simaruba* is greenish, and rich in resins; the outer bark is thin and smooth, shedding or peeling in red sheets or flakes.

Any suitable extracts of *Bursera simaruba* seeds may be used. Suitable extracts may be obtained using conventional methods including, but not limited to, direct extraction of material from the biomass by grinding, macerating, pressing, squeezing, mashing, centrifuging, and/or processes such as cold percolation, agitation/distillation, microwave assisted extraction, sonication, supercritical/subcritical $CO_2$ compressed gas extraction with or without polar modifiers, pressurized solvent extraction, accelerated solvent extraction, pressurized or normal hot water extraction, surfactant assisted pressurized hot water extraction, oil extraction, membrane extraction, Soxhlet extraction, the gold finger distillation/extraction and/or processes disclosed, for example, in U.S. Pat. Nos. 7,442,391, 7,473,435, and 7,537,791 to Integrated Botanical Technologies, LLC, incorporated herein by reference, and the like, or by other methods such as solvent extraction, and the like.

Any of a variety of solvents including polar solvents, non-polar solvents, or combinations of two or more thereof may be used in methods of comprising solvent extraction. Suitable polar solvents include polar inorganic solvents such as water and the like, polar organic solvents such as alcohols and corresponding organic acids, for example C1-C8 alcohols including methanol, ethanol, propanol, butanol, and the like and organic acids, including acetic acid, formic acid, propanoic acid, and the like, polyols and glycols, including C1-C8 polyols/glycols and the like, and combinations of two or more thereof. Suitable non-polar solvents include non-polar organic solvents such as alkanes, including C1-C8 alkanes, cycloalkanes, including C1-C8 alkanes, alkyl ethers, including C1-C8 alkyl ethers, petroleum ethers, ketones, including C1-C8 ketones, methylene chloride, ethyl acetate, xylene, toluene, chloroform, vegetable oil, mineral oil and the like.

In one embodiment, the extract of *Bursera simaruba* seeds is extracted using a solvent selected from the group consisting of C1-C8 alcohols, C1-C8 glycols, liquid carbon dioxide, C5-C8 hydrocarbons, water, and combinations thereof.

In one embodiment extraction may be obtained by non-polar solvents described above or supercritical fluid extraction with or without a polar modifier such as C1-C8 alcohols, water, C1-C8 polyols/glycols or C1-C8 organic acids.

In certain preferred embodiments, the extract of the invention is a polar extract prepared by pulverizing the *Bursera simaruba* seeds and extracting using a polar solvent having a dielectric constant value of between 1 and 100 at 20° C., preferably a dielectric constant of a value between 4 and 60 at 20° C., more preferably a dielectric constant of a value between 4 and 50 at 20° C., and even more preferably a dielectric constant of a value between 4 and 40 at 20° C.

Examples of preferred polar solvents include C1-C8 alcohols, C1-C8 polyols/glycols, C1-C8 organic acids, water and combinations of two or more thereof having a dielectric constant value of between 1 and 100, preferably between 4 and 60, and more preferably between 5 and 40 at 20° C., including, but not limited to, those solvents and combinations of solvents having the desired dielectric constant value as disclosed in "Dielectric Constants of Some Organic Solvent-Water Mixtures at Various Temperatures," Akerlof, Gosta; JACS, Vol. 54, No. 11 (November 1932), pp. 4125-4139, incorporated herein by reference. In certain preferred embodiments, the polar extract is extracted using one or more C1-C8 alcohols, C1-C8 polyols, C1-C8 glycols, and combinations of two or more thereof. In certain more preferred embodiments, the extract is extracted using one or more C1-C4 alcohols, C1-C4 polyols, and/or C1-C4 glycols. In certain more preferred embodiments, the extract is prepared using a solvent comprising methanol, ethanol, or a combination thereof with or without presence of water. In a more preferred embodiment, the extract is prepared using anhydrous alcohol or reagent grade denatured alcohol and *Bursera simaruba* seed, agitating at room temperature for a day. In certain preferred embodiments, the extract may be further refined by charcoal (also referred to as active carbon) treatment.

In certain embodiments, the composition may additionally include extracts from other parts of *Bursera simaruba*, for example, one or more of the bark, leaves, stem, roots, fruits, or flowers. In other embodiments, the composition is essentially free from extracts of other non-seed parts of *Bursera simaruba*.

Any suitable amount of extract of *Bursera simaruba* seeds may be used in the compositions of the present invention. Preferably, the compositions comprise a safe and effective amount of extract of *Bursera simaruba* seeds.

In one embodiment, the amount of extract of *Bursera simaruba* seeds used in a composition of the invention is that effective to achieve an increase in the ceramide levels of 10% according to the test Determination of Ceramide Profile by High-Performance Thin-Layer Chromatography (Assay 5) described herein.

In another embodiment, the amount of extract of *Bursera simaruba* seeds used in a composition of the invention is that effective for providing an increase of hyaluronic acid secretion, preferably greater than a 1.2 fold increase, when measured in accordance with the Hyaluronic acid (HA) Secretion test (Assay 2) described herein.

In certain preferred embodiments, the compositions comprise from greater than zero to about 20% extract of *Bursera simaruba* seeds. In certain other preferred embodiments, the compositions comprise from about 0.0001 to about 20%, from about 0.001 to about 10%, from about 0.01 to about 5%, from about 0.1 to about 5%, or from about 0.2 to about 2% of extract of *Bursera simaruba* seeds. In certain other preferred embodiments, the compositions comprise from greater than zero to about 1%, from about 0.0001 to about 1%, from about 0.001 to about 1%, or from about 0.01 to about 1% of extract of *Bursera simaruba* seeds. In certain other preferred embodiments, the compositions comprise from about 1 to about 5%, preferably from about 2 to about 5%, of extract of *Bursera simaruba* seeds.

Any suitable carrier may be used in the compositions. Preferably, the carrier is a cosmetically-acceptable carrier. As will be recognized by those of skill in the art, cosmetically-acceptable carriers comprise carriers that are suitable for use in contact with the body, in particular the skin, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 99.8% to about 98% of the composition.

The carrier can be in a wide variety of forms. For example, carriers in the form of emulsions, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps.

Examples of suitable cosmetically-acceptable carriers include cosmetically-acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, microneedle patches, bandages, hydrogels, film-forming products, facial and skin masks, make-up, liquid drops, and the like. These product types may contain several types of cosmetically-acceptable carriers including, but not limited to solutions, suspensions, emulsions such as microemulsions and nanoemulsions, gels, solids, liposomes, other encapsulation technologies and the like.

The following are non-limitative examples of carriers. Other carriers can be formulated by those of ordinary skill in the art.

In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99%.

A lotion can be made from such a solution. Lotions typically contain at least one emollient in addition to a solvent. Lotions may comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid or dissolvable substrate (e.g., a wipe, mask, pad, glove or strip).

The compositions of the present invention can also be formulated for use in the oral cavity, such as toothpaste, gel, rinse, solution, patch, and the like. The compositions may also be formulated for use in the eye, such as in solutions, emulsions, suspensions used as drops or washes and the like, or formulated for use in the vaginal mucosa such as via gels, lotions, lubricants, and the like.

The compositions of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like.

Examples of various suitable additional cosmetically acceptable actives include hydroxy acids, benzoyl peroxide, D-panthenol, UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

In certain preferred embodiments, the skin care compositions comprise an extract of *Bursera simaruba* seeds and at least one additional skin moisturizing active agent.

In certain preferred embodiments, the skin care compositions comprise an extract of *Bursera simaruba* and at least one additional agent for improving the signs of aging. Examples of suitable additional agents improving the signs of aging include, but are not limited to, tropoelastin promoters, collagen promoters, retinoids, hyaluronic acid, dimethylaminoethanol, N,N,N',N'-tetrakis(2-hydroxypropyl)ethylenediamine, alpha hydroxy acids, polyhydroxyacids, and combinations of two or more thereof.

"Tropoelastin promoters," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Suitable tropoelastin promoters may be determined, for example, using the TROPOELASTIN PROMOTER ASSAY. The TROPOELASTIN PROMOTER ASSAY is performed as follows. Rat cardiac myoblasts H9C2 (which may be purchased, for example from ATCC of Manassas, Va.) are used. Cultures are maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 ug/ml streptomycin (Invitrogen LifeTechnologies, Carlsbad, Calif.). Cell cultures are transiently transfected with the elastin promoter-luciferase reporter construct (E1p2.2, a 2.2 kb elastin promoter fragment from nt −2267 to nt +2, driving the firefly luciferase gene, which may be obtained from Promega, Madison, Wis.). DNA is prepared by Qiagen Maxi columns (Qiagen Valencia, Calif.). In all transfections, a construct with the thymidine kinase promoter and the Renilla luciferase reporter gene (pRL-TK, Promega, Madison, Wis.) is included as an internal control. Typically, cells grown in 48-well plates are transfected with 0.45 ug total DNA per well using Lipofectamine 2000 (Invitrogen Life Technologies, Carlsbad, Calif.). One day after transfection, cells are treated with agents at indicated concentrations for approximately 24 hours before they are lysed for luciferase assays, using Dual-Luciferase Reporter System from Promega (Madison, Wis.), following manufacturer's protocol. The firefly luciferase activity is measured first (representing elastin promoter activity), followed by the renilla luciferase (internal control), using luminometer LMAX, from Molecular Devices (Sunnyvale, Calif.). The ratio of these two luciferase activities (RLU) is used to evaluate the Tropoelastin Promoter Activity.

The tropoelastin promoter preferably has a Tropoelastin Promoter Activity of at least 1.1, preferably at least 1.25, more preferably at least 1.3, and most preferably at least 1.5, at at least one concentration in the range of 0.5 micrograms/milliliter to 2.5 milligrams per milliliter (on an actives basis), and preferably at at least one concentration in the range of 1.0 micrograms/milliliter to 2.5 milligrams per milliliter (on an actives basis).

Examples of suitable tropoelastin promoters include, but are not limited to, blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "cotinus extract," it is meant an extract of the leaves of "*Cotinus coggygria*," such as a water extract thereof, available from Bilkokoop of Sofia, Bulgaria.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract. One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name "SymMatrix."

Extracts of "*Phyllanthus niruri*" may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev. Preferably, a low molecular weight fraction of *Phyllanthus niruri* is used, for instance a fraction of *Phyllanthus niruri* substantially free of molecular species having a molecular weight of greater than about 100,000 daltons. Preferably, such low molecular weight fraction is water extractable from the *Phyllanthus niruri* plant.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters" according to the present invention include all natural or synthetic compounds that are not retinoids, or derived from retinoids, and are capable of enhancing the production of collagen in the human body.

Suitable collagen promoters may be determined, for example, using the COLLAGEN PROMOTER ASSAY. The COLLAGEN PROMOTER ASSAY is performed as follows. Rat cardiac myoblasts H9C2, which may be purchased from ATCC (Manassas, Va.), are used. Cultures are maintained in Dulbecco's modified Eagle's medium (DMEM, Invitrogen Life Technologies, Carlsbad, Calif.) supplemented with 10% fetal bovine serum, 2 mM glutamine, 100 units/ml penicillin, and 50 ug/ml streptomycin (Invitrogen Life Technologies, Carlsbad, Calif.). Cell cultures are transiently transfected with the Collagen1A promoter-luciferase reporter construct, driving the firefly luciferase gene, which may obtained for example from PREMAS Biotech Pvt. Ltd (Haryana, India). In all transfections, a construct with the thymidine kinase promoter and the Renilla luciferase reporter gene (pRL-TK, Promega, Madison, Wis.) is included as an internal control. Cells grown in 48-well plates are transfected with 0.45 ug total DNA per well using Lipofectamine 2000 (Invitrogen Life Technologies, Carlsbad, Calif.). One day after transfection, cells are treated with agents at the indicated concentrations for approximately 24 hours before they are lysed for luciferase assays, using Dual-Luciferase Reporter System from Promega (Madison, Wis.), following manufacturer's protocol. The firefly luciferase activity is measured first (representing collagen promoter activity), followed by the renilla luciferase (internal control), using luminometer LMAX, from Molecular Devices (Sunnyvale, Calif.). The ratio of these two luciferase activities (RLU) is used to evaluate the activity of each promoter.

Suitable collagen promoters preferably have a Collagen Promoter Activity of at least 1.2, preferably at least 1.25, more preferably at least 1.3; at at least one concentration in the range of 0.5 micrograms/milliliter to 2.5 milligrams per milliliter (on an actives basis), preferably at least one concentration in the range of 1.0 micrograms/milliliter to 2.5 milligrams per milliliter (on an actives basis).

Examples of suitable non-retinoid collagen promoters include, but are not limited to the following: extracts of feverfew (*Tanacetum parthenium*), extracts of *Centella asiatica*, and extracts of *Siegesbeckia orientalis*; extracts of soy; collagen-promoting peptides; ursolic acid; and asiaticoside.

*Centella asiatica*, also known as *Violette marronne* on Reunion Island, Gotu Kola or Indian pennywort in India, *Centella repanda* in North America, and Talapetraka in Madagascar, is a polymorphous herb and belongs to the family of Umbelliferae (Apiaceae), particularly to the Hydrocotyle subfamily. It grows wild throughout the tropics and prefers moist and shady regions at an altitude of about 600 to 1200 meters above sea level. *Centella asiatica* has three varieties: Typica, Abyssinica, and Floridana. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following:

(1) matrikine peptides, (i.e., a peptide derived from the degradation of extracellular matrix proteins—collagen, elastin, or proteoglycan) including palmitoyl pentapeptides, in particular Pal-Lys-Thr-Thr-Lys-Ser-OH, available as MATRIXYL from Sederma (Croda International Group of Edison, N.J.);

(2) GHK copper peptide available as PROCYTE from Photomedex of Montgomeryville, Pa.;

(3) Palmitoyl GHK peptide available as Biopoeptide CL from Sederma (Croda International Group of Edison, N.J.);

(4) Peptides VFTRN, TRNDKL disclosed in EP1775306 B1, and described below in the following formulas I, II and III:

$$R_1\text{-}A1\text{-}A2\text{-}A3\text{-}A4\text{-}A5\text{-}A6\text{-}A7\text{-}A8\text{-}A9\text{-}R_3 \quad (I)$$
$$R_2$$

wherein formula I contains at least six amino acid residues; and:
A1 is Val, Ala, Leu, Met or absent;
A2 is Arg, Lys or absent;
A3 is Phe, Tyr or absent;
A4 is Thr, Ser, Ala, or Lys;
A5 is Arg or Lys;
A6 is Asn, Asp, Gly, or Gln;
A7 is Asp, Asn, Glu, or absent;
A8 is Lys, Arg or absent; and
A9 is Leu, Met, Val, Ile, Phe or absent;
provided that A3 may only be absent if A2 is absent, A2 may only be absent if A1 is absent, A7 may be absent only if A8 is absent, and A8 may only be absent if A9 is absent; each $R_1$ and $R_2$, independently, is H, $C_{1-12}$ alkyl, $C_{7-10}$ phenylalkyl, or C(=O)E1, where E1 is $C_{1-12}$ alkyl, $C_{3-14}$ alkenyl, $C_{3-14}$ alkynyl, phenyl, 3,4-dihydroxyphenylalkyl, naphthyl, or $C_{7-10}$ phenylalkyl; provided that when either $R_1$ or $R_2$ is C(=O)E1, the other must be H; and $R_3$ is OH, $NH_2$, $C_{1-12}$ alkoxy, $C_{7-10}$ phenylalkoxy, $C_{11-14}$ naphthylalkoxy, $C_{1-12}$ alkylamino, $C_{7-10}$ phenylalkylamino, or $C_{11-14}$ naphthylalkylamino; or a cosmetically acceptable salt thereof.

$$R_1\text{-}A'1\text{-}A'2\text{-}A'3\text{-}A'4\text{-}A'5\text{-}A'6\text{-}A'7\text{-}A'8\text{-}A'9\text{-}A'10\text{-}A'11\text{-}R_3 \quad (II)$$
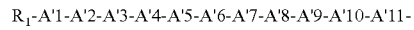
$$R_2$$

wherein formula II contains at least six amino acid residues; and:
A'1 is Val, Ala, Leu or Met;
A'2 is Arg or Lys;
A'3 is Phe or Tyr;
A'4 is Leu, Met, Val, Ile or Phe;
A'5 is His, Tyr or Phe;
A'6 is Ser, Thr, Ala or Lys;
A'7 is Tyr or Phe;
A'8 is Asp, Asn or Glu;
A'9 is Leu, Met, Val, Ile or Phe;
A'10 is Lys or Arg;
A'11 is Asn, Asp, Gly or Gln; and
$R_1$, $R_2$, and $R_3$, are the same as those defined in formula I.

$$R_1-A''1-A''2-A''3-A''4-A''5-A''6-A''7-A''8-A''9-A''10-R_3 \quad (III)$$
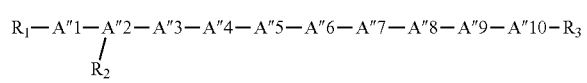
$$R_2$$

wherein formula III contains at least six amino acid residues; and:
A''1 is Cys or Ser;
A''2 is His, Tyr or Phe;
A''3 is Lys or Arg;
A''4 is Leu, Met, Val, Ile or Phe;
A''5 is Leu, Met, Val, Ile or Phe;
A''6 is His, Tyr or Phe;
A''7 is Asn, Asp, Gly or Gln;
A''8 is Val, Ala, Leu or Met;
A''9 is Asn, Asp, Gly or Gln;
A''10 is Lys or Arg; and
$R_1$, $R_2$, and $R_3$, are the same as those defined in formula I.

(5) Biomimetic tetrapeptides, such as those available as Chronoline Tri Peptide from Unipex of Québec, Canada; and (6) Palmitoyl tri-peptide, available as Syn-Coll from DSM of Basel, Switzerland.

Ursolic acid is also known as pentacyclic triterpene acid, Prunol, Malol, Urson, beta-ursolic acid and 3-Beta-Hydroxy-Urs-12-En-28-Oic Acid. It is commercially available for example from Sigma-Aldrich of St. Louis, Mo.

Asiaticoside, also known chemically as: [6-[[3,4-dihydroxy-6-(hydroxymethyl)-5-(3,4,5-trihydroxy-6-methyloxan-2-yl)oxyoxan-2-yl]oxymethyl]-3,4,5-trihydroxyoxan-2-yl] 10,11-dihydroxy-9-(hydroxymethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Santé Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

The compositions of the present invention may comprise additionally at least one skin lightening active agent. Examples of suitable skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea Coposita* root extract, *Saxifraga* extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliants include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, *Portulaca* extract, Licochalcone, chalcone, 2,2'-dihydroxy chalcone, *Primula* extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

Compositions of the present invention may include a cosmetically effective amount of one or more anti-inflammatory compounds. The compositions preferably include, on an active basis, from about 0.1% to about 10%, more preferably from about 0.5% to about 5%, of the anti-inflammatory compound.

Suitable anti-inflammatory active agents include, but are not limited to, compounds that have an IC50 (concentration at which a compound achieves 50% inhibition of inflammation) of less than or equal to 100 μg/ml for Interleukin-2 in the ANTI-INFLAMMATORY ASSAY set forth below. In a preferred embodiment, the IC50 for the second anti-inflammatory compounds is less than about 70 μg/ml, more preferably less than about 50 μg/ml, more preferably less than about 40 μg/ml, more preferably less than about 30 μg/ml.

The ANTI-INFLAMMATORY ASSAY assesses the ability of an agent to reduce the production of cytokines by human lymphocytes stimulated with the T-cell receptor (TCR) activating agent phytohaemagglutinin (PHA), and is conducted in the following manner. Human leukocytes are collected from a healthy adult male via leukopheresis, and adjusted to a density of $1\times10^6$ cells/mL in serum free lymphocyte growth medium (ExVivo-15, Biowhittaker, Walkersville, Md.). PBLs are stimulated with 10 μg/mL PHA in the presence or absence of test samples following published methods (Hamamoto Y., et al. *Exp Dermatol* 2:231-235, 1993). Following a 48 hour incubation at 37° C. with 5% $CO_2$, the supernatant is removed and evaluated for cytokine content using commercially available multiplex cytokine detection kit.

Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following: *Phellodendron amurense* Cortex Extract (PCE), Non-Denatured Soy (*Glycine max*), Feverfew (*Tanacetum parthenium*), Ginger (*Zingiber officinale*), Ginko (*Ginkgo biloba*), Madecassoside (*Centella asiatica* extract ingredient), Cotinus (*Cotinus coggygria*), Butterbur Extract (*Petasites hybridus*), Goji Berry (*Lycium barbarum*), Milk Thistle Extract (*Silybum marianum*), Honeysuckle (*Lonicera japonica*), Basalm of Peru (*Myroxylon pereirae*), Sage (*Salvia officinalis*), Cranberry Extract (*Vaccinium oxycoccos*), Amaranth Oil (*Amaranthus cruentus*), Pomegranate (*Punica granatum*), Yerbe Mate (*Ilex paraguariensis* Leaf Extract), White Lily Flower Extract (*Lilium candidum*), Olive Leaf Extract (*Olea europaea*), Phloretin (apple extract), Oat Flour (*Aveena sativa*), Lifenol (Hops: *Humulus lupulus*) Extract, Bugrane P (*Ononis spinosa*), Licochalcone (Licorice: *Glycyrrhiza inflate* extract ingredient), Symrelief (Bisabolol and Ginger extract), combinations of two or more thereof, and the like.

In one embodiment, the anti-inflammatory agent is a resorcinol. Resorcinol is a dihydroxy phenol compound (i.e., 1,3 dihydroxybenzene) having by the following structure:

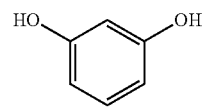

As used herein, "substituted resorcinol" means resorcinol comprising at least one substituent in the 2, 4, 5, or 6 positions. Thus, the substituted resorcinol may have as few as one and as many as four substituents. Positions 1 and 3 of the substituted resorcinol comprise —OH groups, as shown above.

In embodiments wherein substituted resorcinol is used for anti-inflammation, it is highly preferred that all of the substituents of the substituted resorcinol are free of phenyl (—$C_6H_5$ aromatic) moieties. In certain embodiments, all of the substituents are free of aromatic moieties (with or without heteroatoms). In certain such embodiments, it is preferred that all of the substituents of the substituted resorcinol are free of ketone functionalities (carbonyls bonded to two other carbon atoms). In certain other such embodiments, all of the substituents of the substituted resorcinol are free of both phenyl functionalities and ketone functionalities. In certain other such embodiments, the substituted resorcinol comprises at least one substituent comprising 5 to 11 carbon atoms, preferably 5 to 10 carbon atoms, more preferably 5 to 9 carbon atoms, most preferably 5 to 8 carbon atoms. In certain other such embodiments, at least one substituent comprises an alkyl group, such as one having the number of carbon atoms described above. The alkyl group is preferably unsaturated.

In certain embodiments, the 4 position of the resorcinol is substituted, and, in certain embodiments, only the 4 position is substituted. In another embodiment, the 4 position is substituted with an alkyl group. In certain preferred embodiments, the substituted resorcinol comprises a single substituent at the 4 position that comprises an alkyl group. In certain other preferred embodiments, the substituted resorcinol comprises a single substituent at the 4 position that consists of an alkyl group directly bonded to the benzene ring.

Particularly suitable substituted resorcinols include 4-hexyl resorcinol and 4-octylresorcinol, particularly 4-hexyl resorcinol. The structures of 4-hexylresorcinol and 4-octylresorcinol are shown below:

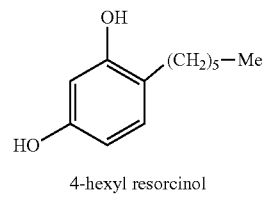

4-hexyl resorcinol

-continued

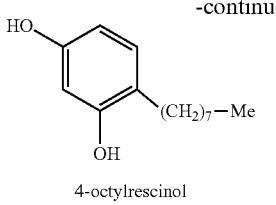

4-octylrescinol

4-Hexyl resorcinol is commercially available as "SYNOVEA HR" from Sytheon of Lincoln Park, N.J. 4-Octylresorcinol is commercially available from City Chemical LLC of West Haven, Conn.

In certain embodiments, the substituted resorcinol comprises at least two substituents in the 2, 4, 5, or 6 positions. Such substituents may optionally be linked to form a ring, such as a cyclic aliphatic hydrocarbon optionally comprising heteroatoms such as sulfur or oxygen. Such a linked substituent may comprise 5 to 10 carbon atoms, e.g., 8 to 10 carbon atoms, and optionally include 1 to 3 heteroatoms. Examples of suitable substituted resorcinols comprising cyclic aliphatic substituents joining the 2 and 3 positions include Zearalanone and β-Zearalanol:

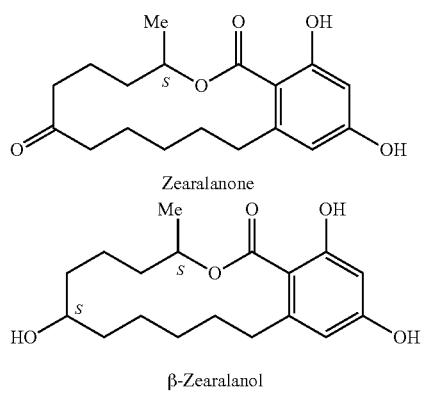

Zearalanone and β-Zearalanol are commercially available from Sigma Chemicals of St. Louis, Mo.

In certain other embodiments, the substituted resorcinol comprises halide-containing and/or nitroso-containing substituents. Suitable examples contain —Cl or —N═O bonded directly to the benzene ring. These substituents may exist for example in the 2 and 4, 2 and 6, or 4 and 6 positions. An example of a dihalide-substituted resorcinol is 2,6-dichlororesorcinol. An example of a dinitroso-substituted resorcinol is 2,4-dinitrososorcinol:

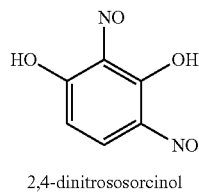

2,4-dinitrososorcinol 2,6-Dichlororesorcinol and 2,4-Dinitrososorcinol are available from City Chemical LLC of West Haven, Conn.

Substituted resorcinols are prepared by means known in the art, for example, using techniques described in U.S. Pat. No. 4,337,370, the contents of which are incorporated herein by reference.

The substituted resorcinols may have any suitable molecular weight. In certain embodiments, the molecular weight of the substituted resorcinol ranges between about 175 and about 300.

By "extracts of feverfew," it is meant extracts of the plant "Tanacetum parthenium," such as may be produced according to the details set for the in US Patent Application Publication No. 2007/0196523, entitled "PARTHENOLIDE FREE BIOACTIVE INGREDIENTS FROM FEVERFEW (TANACETUM PARTHENIUM) AND PROCESSES FOR THEIR PRODUCTION." One particularly suitable feverfew extract is commercially available as about 20% active feverfew, from Integrated Botanical Technologies of Ossining, N.Y.

In the skin care composition of the invention, the ratio of the amounts of the extract of Bursera simaruba seed to the anti-inflammatory compound may be varied. For example, the extract and the anti-inflammatory compound may be present in a weight ratio (which is determined by dividing the amount by weight of the dry extract by the amount by weight of the anti-inflammatory compound) of about 0.001 to about 100, preferably about 0.01 to about 10, more preferably about 0.25 to about 2.

A variety of other materials may also be present in the compositions of the present invention. In certain preferred embodiments, the composition comprises one or more topical ingredients selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β,β-trehalose, α,β-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc New York, N.Y.) and include, but are not limited to anionic surfactants such as sulfates, cationic surfactants such as betaines, amphoteric surfactants such as sodium coco glycinate, noionic surfactants such as alkyl polygucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL."

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of conditioners which impart additional attributes, such as gloss to the hair are suitable for use in this invention. Examples include, but are not limited to, volatile silicone conditioning agent having an atmospheric pressure boiling point less than about 220° C. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable conditioners include cationic polymers, including polyquarterniums, cationic guar, and the like.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

Any fragrance compositions suitable for use on skin may be used in accord with the present invention.

In certain preferred embodiments, the present invention is in the form of a substrate comprising a composition of the present invention. Any suitable substrate may be used. Examples of suitable substrates and substrate materials are disclosed, for example, in U.S. Published Application Nos. 2005/0226834 and 2009/0241242 which are incorporated herein by reference in their entirety.

In certain preferred embodiments, the substrate is a wipe, glove, or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water-insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval. For certain embodiments, the substrate is a glove such as described in U.S. Published Application No 2006/0141014 which is incorporated herein in its entirety. In one embodiment of the invention, the product includes a plurality of water-insoluble substrates of different shapes.

The present invention further comprises a method of improving the barrier function and moisturization of skin by applying to skin in need of improving skin barrier function and moisturization an extract *Bursera simaruba*, in particular an extract of *Bursera simaruba* seeds. The method comprises for example topically applying a composition of the present invention comprising an extract of *Bursera simaruba* to skin in need of improving skin barrier function and moisturization. Such topical application may be to any skin in need of treatment on the body, for example skin of the face, lips, neck, chest, back, arms, axilla, hands, feet and/or legs.

The present invention further comprises a method of improving a sign of skin aging by applying to skin in need of improving the signs of skin aging an extract of *Bursera simaruba*, in particular an extract of *Bursera simaruba* seeds. The method comprises for example topically applying a composition of the present invention comprising an extract of *Bursera simaruba* to skin in need of treatment signs of skin aging. Such topical application may be to any skin in need of treatment on the body, for example skin of the face, lips, neck, chest, back, arms, axilla, hands, feet and/or legs.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like.

In certain embodiments, the methods of the present invention further comprise the step of leaving the *Bursera simaruba* extract in contact with the skin for period of time. For example, in certain preferred embodiments after application, the extract is left in contact with the skin for a period of about 15 minutes or greater. In certain more preferred embodiments, the extract is left in contact with the skin for about 20 minutes or greater, more preferably about 1 hour or greater.

In certain embodiments, the method of the present invention comprises a regimen comprising applying the *Bursera simaruba* extract to skin multiple times over a selected period of time. For example, in certain embodiments, the method comprises applying to skin in need of treatment once or twice daily for at least 12 weeks, preferably at least 8 weeks and more preferably for at least 2 weeks.

In certain preferred embodiments, the methods of the present invention comprise applying at least two different compositions or products comprising a *Bursera simaruba* extract to the skin. For example, the methods may comprise applying a first composition comprising *Bursera simaruba* extract to skin in need of improving skin barrier efficacy and moisturization, followed by applying a second composition comprising *Bursera simaruba* extract that is different from the first composition, to the skin in need of treatment. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, essence, or serum and the other is a facial mask or wipe. In certain other preferred embodiments, at least one of the first and second compositions is a cleanser and the other is a lotion or cream.

The compositions of the present invention may be suitable for a variety of other uses. For example, compositions of the present invention may be useful for skin lightening, cleansing dry skin, treating inflammation, including post-inflammatory hyperpigmentation, for reducing pore size, acne treatment, for reducing sebum production, for scar mitigation and reducing the appearance of stretch marks, for reducing the appearance of cellulite or orange peel appearance. In certain other embodiments, compositions of the present invention may be applied simultaneously with or within several hours of a mechanical or physical exfoliant such as a microdermabrasion treatment, or with a chemical exfoliant or keratolytic agent such as salicylic acid. In certain other embodiments, compositions of the present invention are applied to mucosa or other tissue such as vaginal, oral, or ocular tissue. In certain other embodiments, compositions of the present invention are applied to mild wounds or post-surgical sites to facilitate healing, to insect bites, to poison ivy or similar skin conditions, or in general to mitigate itch. In certain other embodiments, compositions of the present invention are applied to mitigate skin irritations. The irritation may be of external origins caused by ingredients in skin care and cosmetic products such as retinoid and its derivatives, benzoyl peroxide, alpha-hydroxy acids and derivatives thereof, salicylic acid, surfactants, natural plant extracts, sunscreen actives, urea, and preservatives, etc. The irritation may be of other external origins such as the sun, wind, or shaving. The irritation may also be caused by inherent disease conditions such as acne, rosacea, atopic dermatitis, and other disease states. In other embodiments, compositions of the present invention may be useful to reduce redness of the gums. The extracts may further be suitable for use in reducing the appearance of telangiectasia or spider veins, reducing the appearance of rosacea, skin blotchiness, and skin blemishes. In certain embodiments, compositions of the present invention are applied to hair, scalp or both to improve hair health, quality and strength, to promote hair growth or retard hair loss, to prevent or treat dandruff, to prevent or treat seborrhea, seborrheic capitis and to improve scalp health and moisture. In other embodiments, compositions of the present invention are applied to the gum, in the mouth, to prevent or treat gum redness or irritation, to reduce periodontitis, to treat or prevent gingivitis, to reduce the symptoms or feeling of dry mouth. In yet other embodiments, the compositions of the present invention are applied to the eye to treat, prevent or reduce the appearance of red or irritated eye, to prevent or treat conjunctivitis, to improve eye moisture, to reduce the feeling of dry eye. In other embodiments, the compositions of the present invention are applied to the vaginal mucosa to prevent or treat signs of irritation or dryness, loss of firmness.

EXAMPLES

The following test methods were used in the Examples.
Assay 1: PPARδ Transactivation Assay
Control samples of HEK293 transfected with human peroxisome proliferator-activated receptor delta (hPPARδ) ligand binding domain were prepared and harvested as indicated below, but without addition of any extract. Upon treatment, the transactivation of hPPARδ was measured. Cells were lysed and luminescence of the luciferase signal was measured. The potency of the extracts was determined by comparing the fold increase achieved by the extracts against the vehicle-treated control.

Specifically, plasmid containing human PPARδ ligand binding domain (LBD) fused with yeast Gal4 DNA binding domain, and Gal4-luciferase vectors were supplied by Janssen Research & Development, LLC. Human HEK239 cells were grown in DMEM+10% FBS+1% Glutamine+1% Na Pyruvate to about 70% preconfluency in T75 flasks. Cells were transiently transfected with two plasmids (1:1 ratio) using Lipofectamin 2000 reagent (Life technologies, Grand Island, N.Y.) in T75 flask. The transfection protocol for a T75 flask included treating cells with 1) bug DNA (5 ug of each vector)+1.25 mL OptiMEM; 2) 25 ul lipofectamine+1.25 mL OptiMEM; 3) incubating for 5 min; 4) mixing together; 5) incubating 20 min; and 6) adding to 10 mL growth media without P/S. After 20-24 h transfection, media were removed and cells were lifted and counted. Compound treatment was prepared in phenol-red free growth media with 0.1% final DMSO concentration (vehicle) and then added into designated 96 well plates. 40,000 cells were added onto each well in additional 100 ul of phenol-red free growth media. Final volume for each reaction was 200 ul. Following 20-24 h treatment, media were removed and kept for LDH assay. 25 ul of 1×PLB lysis buffer was added in each well and incubated for 10 min with gentle shaking. 100 ul of luciferase detection buffer (Promega luciferase assay system Cat #E1501) was added to measure luciferase activity.

Assay 2: PPARα Transactivation Assay
hPPARα transactivation activity was measured by luciferase assay using hPPARα assay kit (Cat #IB00111) from INDIGO biosciences (State College, Pa.) and the manufacturer's instructions for the assay were followed. In brief, test materials were prepared at the appropriate dilution series of 2×-concentrated reference agonist (GW590735) and an appropriate dilution series of 2×-concentrated test material(s) to be assayed in compound screening media (supplied in the kit). 10 mL of cell recovery media (supplied in the kit) was added to frozen cell pellet (hPPARα cells) and defrosted at a water bath. 100 ul of hPPARα cells and prepared test materials were dispensed into each well of the 96 well assay plate (final volume was 200 ul per well).

Following an overnight incubation, the treatment media were discarded and 100 ul of Luciferase Detection Reagent (LDR, supplied) was added per well. The intensity of light emission from each sample well was quantified using a plate-reading luminometer (SpectraMax).

Assay 3: Gene Expression
Samples were isolated from primary human keratinocytes and skin equivalents that had been treated with extracts dissolved in DMSO or DMSO without extracts (as control) for 24 hours using Qiagen RNeasy kit with DNase I digestion (Cat #79254) (Valencia, Calif.). Reverse transcription was performed using High Capacity cDNA kit (Life technologies Cat #4368814). 40 to 60 ng of cDNA samples were used for QPCR reaction. Taqman gene expression assay was purchased from Life Technologies (Grand Island, N.Y.). QPCR reaction was performed using ABI 7500 fast amplifier. The PCR primers used are presented in Table 1. All gene expression data were normalized by reference genes, polymerase (RNA) II polypeptide A (POLR2A) or/and ribosomal protein, large, PO (RPLPO). Relative gene expression was calculated by comparative CT method.

Carnitine palmitoyltransferase I (CPT1) is a mitochondrial enzyme, part of a family of enzymes called carnitine acyltransferases that mediate the transport of long-chain fatty acids across the membrane by binding them to carnitine for further lipid oxidation.

Together with other genes like ANGPTL4 are targets of PPARα/δ activation; in other words their expression is increased once the PPAR receptors are activated by their ligands.

Involucrin is a protein of human epidermis encoded by the IVL gene and it contributes to the cell envelope formation that protects corneocytes in the skin.

Transglutaminase catalyzes the formation of bonds between a free amine group and the gamma-carboxamide group of glutamine that exhibit high resistance to proteolytic degradation and enhance the natural barrier of the skin.

Sphingomyelin phosphodiesterase 3 is an enzyme that in humans is encoded by the SMPD3 gene and is involved in ceramide synthesis. Ceramide glucosyltransferase (UGCG) converts ceramides to glucosylceramides for transport. Elongation of very long chain fatty acids 4 (ELOVL4) is required for very long chain fatty acids synthesis, which are a major component of ceramides.

Claudin 17 belongs to a family of proteins that are the most important components of the tight junctions that control the flow of molecules in the intercellular space between the cells of the epidermis.

TABLE 1

PCR primers
Life Technologies (Applied Biosystems)

| Gene Symbol | Catalog Number |
|---|---|
| ANGPTL4 | Hs01101127_m1 |
| CPT1A | Hs00912671_m1 |
| PPARδ | Hs04187066_g1 |
| IVL (Involucrin) | Hs00846307_s1 |
| TGM1 | Hs01070310_m1 |
| CLDN17 | Hs01043467_s1 |
| SMPD3 | Hs00920354_m1 |
| GBA | Hs00986836_g1 |
| UGCG | Hs00234293_m1 |
| ELOVL4 | Hs00224122_m1 |
| POLR2A | Hs00172187_m1 |

Assay 4: Hyaluronic Acid (HA) Secretion

Human dermal fibroblasts were maintained in flask in growth medium consisting of DMEM plus 10% fetal bovine serum, 50 units/ml penicillin and 50 µg/ml streptomycin. Cells were seeded at 20,000 cells per well in a 96 well plate. After 24 hours incubation, cells were treated with test articles dissolved in DMSO or DMSO without extracts (as control) prepared in DMEM+2% FBS. Culture media was collected at 48 hours post-treatment, and measured for HA (Hyaluronic acid) secretion using Hyaluronan ELISA kit (Echelon, cat. #K-1200) following the manufacturer protocol. To assess activity, the colorimetric chance was measured at 405 nm and the results expressed as a fold change over untreated controls.

Assay 5: Hyaluronidase Enzyme Inhibition

The measurement of the hyaluronidase inhibition activity was performed using an assay from Sigma ("Enzymatic Assay of HYALURONIDASE", Revised: Apr. 1, 1996, SSHYAL01) with the following modifications. The ability of test samples to inhibit the enzyme hyaluronidase (EC 3.2.1.35) was performed in 96-well plate by mixing the samples (25 µl at various concentrations) with hyaluronidase (Sigma, H3506, 25 µl at 20 µ/ml), and incubated at 37° C. for 10 min. This mixture was then combined with 50 µl HA substrate (Sigma Prod. No. H-7630, at 0.03%) and incubated at 37° C. for 45 min. Then 100 µl of an acidic buffer (pH 3.75) was added to the mixture and allowed to stand for 10 min. The turbidity of the undigested HA in the mixture was measured at 540 nm using a microplate reader (Versamax, Molecular Devices, Sunnyvale, Calif.).

Estimation of hyaluronidase inhibition activity:

HYAL activity=Transmittance (sample/HA)−Transmittance (sample/HYAL/HA) Transmittance (sample/HA)

HYAL-IA (%)=(1−HYAL activity)*100

Assay 6: Extra-Cellular Matrix Gene Expression

Changes in the transcription of extra-cellular matrix genes were measured by quantitative polymerase chain reaction (qPCR) assays. Dermal fibroblasts and epidermal skin equivalents were treated with extracts dissolved in DMSO or with DMSO alone (as control) in prepared media for 24 hours prior to mRNA extraction. The mRNA of primary human dermal fibroblasts and epidermal skin equivalents (MatTak, Epi-FT-200) were isolated using the RNeasy Mini Kit (250), (Qiagen Catalog #74106). The mRNA was reverse transcribed to complementary DNA (cDNA) using SuperScript III First Stand, (Invitrogen Catalog #18080-400). The qPCR analysis was performed using Power SYBR Green PCR Master Mix, (Applied Biosystems Catalog #4367659), and run on a 7500 Real Time PCR system (Applied Biosystems) using the following conditions: 95° C. for 15 seconds, 60° C. for 1 minute with 40 cycles.

The primers of target genes are listed in Table 2 below. The potency of the test compounds was determined by comparing the fold change achieved by the test compounds against the control.

TABLE 2

Primers for PCR assays

| Gene | Gene Symbol | SABiosciences/ QIAGEN Catalog Number |
|---|---|---|
| Collagen VII | COL7A1 | PPH01968A |
| Elastin | ELN | PPH06895F-200 |
| Hyaluronan synthase 2 | HAS2 | PPH13147A |
| Hyaluronan synthase 3 | HAS3 | PPH10335E |

Assay 7—Determination of Ceramide Profile by High-Performance Thin-Layer Chromatography Sample Extraction and Condensation Skin equivalents or $0.5-1 \times 10^6$ cells were homogenized with 2 mL chloroform:methanol (2:1) and transferred to a vial containing 1 mL Phosphate-Buffered Saline Solution. Homogenizer was rinsed with 2 2 mL portions of chloroform:methanol (2:1) and the rinses were added to the vial containing the extract and the PBS. The mixture was vortexed and the phases were allowed to separate. The organic phase was evaporated to dryness under vacuum. Sample residue dissolved in 200 uL chloroform:methanol (2:1)

High-Performance Thin-Layer Chromatography

The residue was dissolved in 200 uL chloroform:methanol (2:1). Twenty microliters and 40 uL of sample solution was applied on the HPTLC plate (Whatman Partisil) using CAMAG Automatic TLC Sampler 4 and separated using the following sequential development system: (1) dichloromethane:ethyl acetate:acetone (80:16:4), (2) chloroform:methanol:acetone (76:16:8), and (3) hexane:chloroform:acetic acid:acetone:methanol (6:80:0.1:10:4). The plates were stained with 3% copper acetate in 8% phosphoric acid and charred at 160° C.

Quantification

Samples were applied in parallel for positional corrections and compared to a similarly prepared blank extract (tape strip without exposure to skin lipids). Quantification was performed against known quantities of Ceramide III standard (Cosmoferm) by densitometry (CAMAG).

The following examples illustrate the preparation and efficacy of *Bursera simaruba* extracts.

Example 1: Preparation of Polar *Bursera Simaruba* Seed Extract (E1)

*Bursera simaruba* seed was collected in Florida, USA. Species identification was based on gross morphological characteristics using A. Gentry, A Field Guide to the Families and Genera of Woody Plants of Northwest South America; Conservation International, Washington, D.C.; pp. 299-302. Approximately 10 g of ripe, hulled seed was homogenized in a blender with 10 mL of 80% aqueous methanol, and the suspension maintained in constant motion for 2 hours. The resulting suspension was filtered and dried under low pressure using a rotary evaporator not exceeding 40° C. The plant material remaining after the extraction of the soluble components was re-suspended in the extraction medium and maintained in constant motion. After 24 hours, the suspension was filtered and dried under low pressure using a rotary evaporator not exceeding 40° C. The combined dry mass from the 80% aqueous methanol extraction totaled approximately 340 mg (E1), for a yield of 3.4%.

Example 2: Preparation of Non-Polar *Bursera Simaruba* Seed Extract (E2)

*Bursera simaruba* seed was collected as described in Example 1. Approximately 10 g of ripe, hulled seed was homogenized in a blender with 10 mL of pure chloroform, and the suspension maintained in constant motion for 2 hours. The resulting suspension was filtered and dried under low pressure using a rotary evaporator not exceeding 40° C. The plant material remaining after the extraction of the soluble components was re-suspended in the extraction medium and maintained in constant motion. After 24 hours, the suspension was filtered and dried under low pressure using a rotary evaporator not exceeding 40° C. The combined solvent-free oily matter from the chloroform extraction totaled approximately 3 grams (E2), for a yield of 30%.

Example 3: Preparation of Polar *Bursera Simaruba* Bark Extracts (E3 and E4)

*Bursera simaruba* bark was collected in Florida, USA. Approximately 3 gram of the red, peeling outer bark was ground to a fine powder and suspended in 30 mL of reagent grade water and maintained in constant motion for 5 hours. A second 3 gram batch of bark was ground to a fine powder and suspended in 30 mL of reagent grade methanol and maintained in constant motion for 5 hours. The resulting suspensions were filtered and dried separately under low pressure using a rotary evaporator not exceeding 40° C. The plant material remaining after the extraction of the soluble components from each was re-suspended in the respective extraction media and maintained in constant motion. After 24 hours, the suspensions were filtered and dried under low pressure using a rotary evaporator not exceeding 40° C. The combined dry mass from the water extraction totaled approximately 140 mg (E3), for a yield of 4.7% and the combined dry mass from the methanol extraction totaled approximately 100 mg (E4), for a yield of 3.3%.

Example 4

Samples of Extracts E1, E2, E3 and E4 were compared for transactivation of hPPARδ using the method of Assay 1.

The results are shown in Table 3.

TABLE 3

| PPARδ activation over vehicle control | | |
|---|---|---|
| Test article | Concentration | Fold change |
| Untreated cells | | 1.0 |
| E1 | 50 µg/mL | 8.9 |
| E1 | 25 µg/mL | 3.38 |
| E1 | 5 µg/mL | 2.27 |
| E1 | 1 µg/mL | 1.79 |
| E2 | 50 µg/mL | 2.97 |
| E2 | 25 µg/mL | 2.78 |
| E2 | 5 µg/mL | 2.03 |
| E2 | 1 µg/mL | 1.31 |
| E3 | 50 µg/mL | 1.0 |
| E4 | 50 µg/mL | 1.0 |

Example 5

Samples of Extracts E1, E2, E3 and E4 were compared for transactivation of PPARα using the method of Assay 2.

The results are shown in Table 4.

TABLE 4

| PPARα activation over vehicle control | | |
|---|---|---|
| Test article | Concentration | fold change |
| Untreated cells | | 1 |
| E1 | 50 µg/mL | 9 |
| E1 | 25 µg/mL | 10.31 |
| E1 | 5 µg/mL | 3.86 |
| E1 | 1 µg/mL | 1.91 |
| E2 | 50 µg/mL | nt |
| E2 | 25 µg/mL | 2.48 |
| E2 | 5 µg/mL | 2.64 |
| E2 | 1 µg/mL | 1.33 |

Examples 4 and 5 show the ability of the extracts of *Bursera simaruba* seeds (E1 and E2) to increase the transactivation of both PPARα and PPARδ. These assays were used as screening assays for the remaining barrier-related assays. The bark extracts (E3 and E4) were not active, and therefore were not assayed further.

Example 6: Transcription of Ceramide Synthesis Genes, Differentiation Markers, and PPAR Target Genes Extract E1 was tested for increase in ceramide synthesis gene transcription, differentiation markers and PPAR target genes in accord with the method of Assay 3 described above and the results are given in Tables 5-8 below.

TABLE 5

Results of PCR experiments using human keratinocyte cell culture showing results for PPARδ and target genes.

|  |  | ANGPTL4 | | CPT1A | | PPARδ | |
| --- | --- | --- | --- | --- | --- | --- | --- |
| Extract | Concentration (μg/mL) | Fold Change | Std Dev | Fold Change | Std Dev | Fold Change | Std Dev |
| Control |  | 1 | 0.1 | 1 | 0.1 | 1 | 0.1 |
| E1 | 1 | 6.6 | 1.6 | 1.4 | 0.1 | 6.9 | 0.8 |
| E1 | 5 | 6.4 | 0.8 | 1.6 | 0.3 | 9.5 | 1.2 |
| E1 | 25 | 14.2 | 0.9 | 2.1 | 0.2 | 17.2 | 1.6 |

TABLE 6

Results of PCR experiments using human keratinocyte cell culture showing results for cellular differentiation markers

|  |  | INV | | TGM1 | | CLDN17 | |
| --- | --- | --- | --- | --- | --- | --- | --- |
| Extract | Concentration (μg/mL) | Fold Change | Std Dev | Fold Change | Std Dev | Fold Change | Std Dev |
| Control |  | 1 | 0.2 | 1 | 0.1 | 1 | 0.1 |
| E1 | 1 | 5.8 | 0.6 | 3.8 | 0.9 | 81.4 | 18.3 |
| E1 | 5 | 7.3 | 1.3 | 4.9 | 2 | 118.5 | 19.3 |
| E1 | 25 | 9.3 | 1.4 | 4.8 | 1.1 | 101.9 | 10.6 |

TABLE 7

Results of PCR experiments using human keratinocyte cell culture showing results for ceramide synthesis genes

|  |  | SMPD3 | | GBA | |
| --- | --- | --- | --- | --- | --- |
| Extract | Concentration (μg/mL) | Fold Change | Std Dev | Fold Change | Std Dev |
| Control |  | 1 | 0.2 | 1 | 0.1 |
| E1 | 1 | 4.5 | 0.5 | 6.5 | 1 |
| E1 | 5 | 7.1 | 2.1 | 8.3 | 1.6 |
| E1 | 25 | 12.1 | 3.3 | 10 | 0.5 |

TABLE 8

Results of PCR experiments using epidermal skin equivalents

| Extract | Concentration (mg/mL) | ANGPTL4 Fold Change | UGCG Fold Change | Involucrin Fold Change | ELOVL4 Fold Change | CLDN17 Fold Change |
| --- | --- | --- | --- | --- | --- | --- |
| Control |  | 1 | 1 | 1 | 1 | 1 |
| E1 | 5 | 1.4 | 3.9 | 7.1 | 2.2 | 5.1 |
| E1 | 10 | 2.7 | 3.3 | 4.9 | 2.8 | 14.0 |
| E1 | 20 | 2.5 | 3.0 | 2.0 | 2.1 | 9.9 |

This example demonstrates the ability of the *Bursera simaruba* seed extracts to induce expression of ceramide synthesis genes and skin differentiation related genes, which demonstrate an ability to induce physiological changes that positively affect skin barrier function and would be expected to improve the moisturization of skin and improve the appearance of dry skin including reducing the appearance of skin flakes.

Example 7: Determination of Ceramides in Human Primary Keratinocytes

Extract E1 was tested for ceramide levels using the method of Assay 7 described above. The results are given in Table 9 below.

TABLE 9

Increase in ceramide levels

| Extract | Concentration (μg/mL) | Percentage change over control (100%) |
| --- | --- | --- |
| E1 | 25 | 175.7 |
| E1 | 25 | 210.4 |
| E1 | 25 | 114.3 |

Example 8: Hyaluronic Acid (HA) Secretion

Extracts E1, E2 and E4 were tested for hyaluronic acid secretion using the method of Assay 4 described above. The results are given in Table 10 below.

TABLE 10

Increase in hyaluronic acid secretion

| Extract | Concentration (μg/mL) | Fold change |
| --- | --- | --- |
| Control |  | 1 |
| E1 | 0.2 | 1.1 |
| E1 | 0.5 | 2.1 |
| E2 | 5 | 1.3 |
| E4 | 5 | 2.5 |

Example 9: Hyaluronidase Enzyme Inhibition Activity Assay

Extracts E1, E3 and E4 were tested for hyaluronidase enzyme inhibition activity in accord with the method of Assay 5 above. The results are given in Table 11 below.

TABLE 11

Inhibition of hyaluronidase enzyme

| Extract | Concentration (mg/mL) | % inhibition |
| --- | --- | --- |
| E1 | 0.5 | 54 |
| E3 | 0.5 | 98 |
| E4 | 0.5 | 95 |

Example 10: Transcription of Extra-Cellular Matrix Genes

Extracts E1 and E2 were tested for changes in transcription of extra-cellular matrix genes in accord with the method of Assay 6 above. The results are given in the Tables 12 and 13.

TABLE 12

Results from PCR analysis of Dermal fibroblast cell culture

| Extract | Concentration (µg/mL) | Collagen 7 Fold Change | HAS2 Fold Change |
|---|---|---|---|
| Control | | 1.00 | 1.00 |
| E1 | 0.5 | 1.5 | 4.5 |
| E2 | 5 | 1.1 | 2.3 |

TABLE 13

Results from PCR analysis of epidermal skin equivalents

| Extract | Concentration (mg/mL) | Col7A1 Fold Change | Elastin Fold Change | HAS2 Fold Change | HAS3 Fold Change |
|---|---|---|---|---|---|
| Control | | 1.00 | 1.00 | 1.00 | 1.00 |
| E1 | 5 | 2.4 | 0.2 | 1.0 | 2.8 |
| E1 | 10 | 2.0 | 0.7 | 0.7 | 3.4 |
| E1 | 20 | 1.4 | 1.9 | 2.3 | 3.5 |
| E1 | 50 | 5.8 | 12.7 | 17.0 | 6.0 |

The preceding examples 8-10 demonstrate the ability of the *Bursera simaruba* seed extracts (E1 and E2) to induce expression of extracellular matrix genes, enzymes which produce extracellular matrix expression, and production of hyaluronic acid. Collectively these results demonstrate an ability of *Bursera simaruba* seed extracts to induce biological benefits which would be expected to improve the appearance of skin wrinkles, fine lines, sagging or lax skin and aged skin.

Example 11: Compositions Containing *Bursera Simaruba* Extract

A skin care composition according to the invention was prepared using the ingredients shown in Table 14.

TABLE 14

| Trade Name | INCI Name | % weight |
|---|---|---|
| Deionized Water | Water | 70.64 |
| Sodium Chloride | Sodium Chloride | 0.01 |
| Extract E1 | | 1.00 |
| Snow White Petrolatum | Petrolatum | 4.00 |
| ISOFOL 28 | Dodecylhexadecanol | 2.50 |
| DOW CORNING Q7-9120 (20 CS) | Dimethicone | 1.25 |
| KESSCO IPP | Isopropyl Palmitate | 3.00 |
| VARISOFT TA-100 | Distearyldimonium Chloride | 5.00 |
| Glycerin | Glycerin | 12.00 |
| Benzyl Alcohol | Benzyl Alcohol | 0.60 |

The composition shown in Table 14 was prepared as follows: water was added to a process vessel. Mixing was begun and salt was added and mixed until dissolved. Heat was applied and mixing continued until 85° C. was reached. Glycerin was then added while mixing continued while temperature was maintained at 85° C. VARISOFT TA 100 was added, as was petrolatum and ISOFOL 28, DC Q7-9120 20 cs., and isopropyl palmitate. The composition was mixed at 85° C. for another 10-15 minutes. E1 was added to the mixture. The composition was then removed from heat and continued to mix and cooled. At 40° C., benzyl alcohol was added, q.s. with water and continue to mix and cool to 30-35° C. The composition was then filled into packaging.

A skin care composition according to the invention was prepared using the ingredients shown in Table 15.

TABLE 15

| Trade Name | INCI Name | % weight |
|---|---|---|
| Deionized Water | Water | 65.55 |
| Extract E1 | | 5.00 |
| Snow White Petrolatum | Petrolatum | 4.00 |
| ISOFOL 28 | Dodecylhexadecanol | 2.50 |
| DOW CORNING Q7-9120 (20 CS) | Dimethicone | 1.25 |
| KESSCO IPP | Isopropyl Palmitate | 3.00 |
| VARISOFT TA-100 | Distearyldimonium Chloride | 5.00 |
| Glycerin | Glycerin | 12.00 |
| BHT | BHT | 0.10 |
| Retinol 10S | *Glycine Soja* (Soybean) Oil and Retinol | 1.00 |
| Benzyl Alcohol | Benzyl Alcohol | 0.60 |

The composition shown in Table 15 was prepared as follows. Water was added to a process vessel and the temperature was set to 85° C. Mixing was begun and glycerin was added and mixed until dissolved. VARISOFT TA-100 and Petrolatum were added and ISOFOL 28, DC Q7-9120 20 cs., and isopropyl palmitate. The composition was mixed at 85° C. for another 10-15 minutes. The composition was then removed from heat and Retinol 10S and Extract E1 were added to the mix and cooled. At 40° C., benzyl alcohol was added, q.s. with water and continue to mix and cool to 30-35° C. The composition was then filled into packaging.

A skin care composition according to the invention was prepared using the ingredients shown in Table 16.

TABLE 16

| Trade Name | INCI Name | % weight |
|---|---|---|
| Purified water | Deionized Water | 77.90 |
| Extract E1 | | 0.10 |
| HYDROLITE 5 | Pentylene glycol | 5.00 |
| NATRULON OSF | *Carthamus Tinctorius* Oleosome | 10.00 |
| FINSOLV TN | C12-15 Alkyl Benzoate | 4.00 |
| ARISTOFLEX AVC | Ammonium Acryloyldimethyl-taurate/VP Copolymer | 2.00 |
| *Tanacetum parthenium* extract | *Chrysanthemum Parthenium* (Feverfew) Leaf/Flower/Stem Juice | 1.00 |

The composition shown in Table 16 was prepared as follows. Extract E1 was weighed and dissolved in HYDROLITE 5 and deionized water was added to form Phase A. NATRULON OSF and FINSOLV TN were mixed to form Phase B. Phase B was added to Phase A very slowly under continuous mixing. Mixing was continued for 15 minutes until a uniform emulsion was formed. ARISTOFLEX was added to the emulsion under continuous mixing at high speed to obtain a thick, smooth and homogenous formulation.

A skin care composition according to the invention was prepared using the ingredients shown in Table 17.

TABLE 17

| Trade Name | INCI Name | % weight |
|---|---|---|
| Purified water | Water | 66.95 |
| Extract E1 | | 1.00 |
| Carbomer | Cross-linked polyacrylic acid | 0.60 |
| VERSENE NA | Disodium EDTA | 0.20 |

TABLE 17-continued

| Trade Name | INCI Name | % weight |
|---|---|---|
| Brij 72 | Steareth-2 | 0.75 |
| Brij 721 | Steareth-21 | 1.50 |
| FINSOLV TN | C12-15 Alkyl Benzoate | 2.00 |
| Dimethicone | Dow Corning Q7-9120 Silicone Fluid (20 cst) | 5.00 |
| Phenonip XB | Phenonip XB | 1.00 |
| LYS' LASTINE | *Peucedanum graveolens* (10% active) | 10.00 |
| SYMMATRIX | Maltodextrin, *Rubus Fruticosus* (Blackberry) Leaf Extract (10% active) | 10.00 |
| Glycerin | Glycerin | 1.00 |

The composition shown in Table 17 was prepared as follows. An oil phase was prepared by adding FINSOLV TN to a clean glass beaker. Agitation was begun and the vessel was heated to 55-60° C. When the oil phase reached 55 C or higher, Brij 72 and Brij 721 were added. When the oil phase reached 55-60° C., it was held at that temperature and mixed for 15 min (or until uniform). The temperature was then held at 55-60° C. with mixing until addition to water phase. A water phase was prepared by adding water to a clean glass beaker. Agitation was begun and the vessel was heated to 55-60° C. Disodium EDTA was added. At 55-60° C., the ingredients were mixed for 15 min or until homogeneous. The temperature was then held at 55-60° C. with mixing for phasing. The oil phase was added to the water phase with increased agitation and then mixed at high speed for 10-20 min. At 50° C. or lower, dimethicone was added. At 40° C. or lower, Phenonip XB was added. The phases were then mixed for 10 min or until uniform. Sodium hydroxide was added (target pH was 5.4). The composition was then mixed for 10 min or until uniform. LYSLASTINE and SYMMATRIX were then added. Extract E1 was weighed and dissolved in Glycerin and added to the mixture. This was mixed until uniform. Water was then added to QS and the composition was then mixed for 10 minutes.

What is claimed is:

1. A skin care composition comprising an extract of hulled *Bursera simaruba* seeds and a cosmetically acceptable topical carrier, wherein said composition comprises from about 0.0001 to about 20% of said extract and wherein said cosmetically acceptable topical carrier is an emulsion.

2. The skin care composition of claim 1, wherein the composition comprises from about 0.01 to about 5% of said extract.

3. The skin care composition of claim 1, wherein said cosmetically acceptable topical carrier comprises a topical ingredient selected from the group consisting of surfactants, chelating agents, emollients, humectants, conditioners, preservatives, opacifiers, fragrances, and combinations thereof.

4. The skin care composition of claim 1, wherein said extract of *Bursera simaruba* seeds is extracted using a solvent selected from the group consisting of $C_1$-$C_8$ alcohols, $C_1$-$C_8$ glycols, liquid carbon dioxide, $C_5$-$C_8$ hydrocarbons, water, and combinations thereof.

5. The skin care composition of claim 4, wherein said solvent is selected from the group consisting of water, ethanol, methanol, liquid carbon dioxide and combinations thereof.

6. The skin care composition of claim 1, further comprising a skin moisturizing agent.

7. The skin care composition of claim 1, further comprising an anti-aging agent.

8. The skin care composition of claim 1, wherein the composition is combined with a wipe, a mask, and combinations thereof.

9. The skin care composition of claim 1, further comprising at least one of glycerin, petrolatum, isopropyl palmitate, and dimethicone.

10. The skin care composition of claim 1, wherein the composition further comprises glycerin.

11. The skin care composition of claim 1, further comprising an extract of *Tanacetum parthenium*.

* * * * *